United States Patent [19]
Herkes

[11] Patent Number: 5,902,883
[45] Date of Patent: May 11, 1999

[54] CYANOBUTYLATION OF AMMONIA, ALKYLAMINES AND HYDRAZINE WITH 3-PENTENENITRILE, 4-PENTENENITRILE OR MIXTURES THEREOF

[75] Inventor: Frank Edward Herkes, Wilmington, Del.

[73] Assignee: E. I. du Pont de Nemours and Company, Wilmington, Del.

[21] Appl. No.: 08/993,967

[22] Filed: Dec. 18, 1997

[51] Int. Cl.[6] .................... C07D 241/04; C07C 255/00

[52] U.S. Cl. ............................... 544/402; 558/452

[58] Field of Search .............. 558/452; 544/402

[56] References Cited

U.S. PATENT DOCUMENTS

| 4,211,725 | 7/1980 | Kluger et al. | 260/583 P |
|---|---|---|---|
| 4,260,556 | 4/1981 | Kluger et al. | 260/465.5 R |
| 4,496,474 | 1/1985 | Reck | 252/311.5 |
| 5,070,202 | 12/1991 | Herkes | 544/402 |

OTHER PUBLICATIONS

March, J., "Advanced Organic Chemistry", 4th ed., p. 768 1992.

*Primary Examiner*—Johann Richter
*Assistant Examiner*—Joseph Murray

[57] ABSTRACT

The present invention relates to a process for the cyanobutylation of ammonia, an alkylamine or hydrazine with 3- and 4-pentenenitrile and mixtures thereof to form alkylaminonitriles.

10 Claims, No Drawings

CYANOBUTYLATION OF AMMONIA, ALKYLAMINES AND HYDRAZINE WITH 3-PENTENENITRILE, 4-PENTENENITRILE OR MIXTURES THEREOF The present invention relates to a process for the cyanobutylation of ammonia, primary and secondary alkylamines and hydrazine with 3- and 4-pentenenitrile and mixtures thereof to form alkylaminonitriles. The aminonitriles or alkylaminonitriles formed by the process of the present invention can be hydrogenated to form alkyldiamines.

BACKGROUND OF THE INVENTION

U.S. Pat. Nos. 4,260,556 and 4,211,725 teach reaction of 2-pentenenitrile with ammonia or ethylenediamine to produce alkylaminonitriles. U.S. Pat. No. 4,496,474 teaches the reaction of 2-pentenenitrile with alkylamines having from 8 to 22 carbons to produce the corresponding nitrile compound. U.S. Pat. No. 5,070,202 teaches a process having improved reaction rate and selectivity in the reaction of 2-pentenenitrile with amines to form alkylaminonitriles by the incorporation of from 15 to 60 weight percent water in the reaction mixture.

It has now been found that alkylaminonitriles can be made with high yields and selectivities using 3-pentenenitrile, 4-pentenenitrile and mixtures of these isomers.

SUMMARY OF THE INVENTION

The present invention is a process for making aliphatic aminonitriles comprising the steps of forming a reaction mixture comprising 3-pentenenitrile, 4-pentenenitrile or mixtures of 3-pentenenitrile and 4-pentenenitrile and ammonia, an alkylamine or hydrazine, or optionally forming the reaction mixture in the presence of water or incorporating water into the reaction mixture; and reacting the mixture at a temperature from about 25 to 200° C. and at pressures from autogeneous to pressures of about 1500 psig. 1500 psig.

The reaction rate of the process may be increased by the addition of a strong base such as a water soluble alkali metal hydroxide, an alkaline earth metal hydroxide, a tertiary amine, for example, 1,3-di-methylpiperidine, triethylamine and pyridine, a Lewis base, a strongly basic ion exchange resin, a basic alumina or zeolite.

The present process may also be carried out with a solvent present in the reaction mixture. The solvent may be used alone or in combination with water. The preferred concentration of water in the reaction mixture is from 15 to 60% by weight.

The weight ratio of 3-pentenenitrile to 4-pentenenitrile in the present process may be from 0 to 1 to 1 to 0.

The present process may be run as a continuous or a batch process.

DETAILED DESCRIPTION

The present invention is a process for making aliphatic aminonitriles comprising the steps of forming a reaction mixture comprising 3-pentenenitrile, 4-pentenenitrile or mixtures of 3-pentenenitrile and 4-pentenenitrile and ammonia, an alkylamine or hydrazine, or optionally forming the reaction mixture in the presence of water or incorporating water into the reaction mixture; and reacting the mixture at a temperature from about 25 to 200° C.

The present process is suited for cyanobutylation of both primary and secondary amines, and accordingly as used herein the term alkylamine includes both primary and secondary amines.

Aminonitriles formed in the present process from the reaction of the subject pentenenitriles with ammonia, alkylamines or hydrazine are useful as starting materials for making various polymer classes. For example, the product aminonitrile formed when ammonia or hydrazine is reacted with the subject pentenenitriles according to the present process may be hydrogenated to form 1,3-pentanediamine. 1,3-pentanediamine has a variety of uses such as use a monomer for forming polymers including polyamides, polyimides and polyurethanes-polyureas. 1,3-pentanediamine may be used as a chain extender, a metal chelating agent or as an epoxy curing agent.

To form the diamine from the animonitrile products of the present invention, the amoninitrile is usually hydrogenated. Typically such hydrogenations are carried out over metal catalysts such as RANEY nickel, RANEY cobalt, RANEY nickel or RANEY cobalt catalysts promoted with chromium, nickel, iron, molybdenum or mixtures of any of these metals (RANEY is a trademark of W. R. Grace and Company), supported nickel or cobalt catalysts, palladium, platinum, ruthenium or iron catalysts. The hydrogenation is typically run at temperatures of from about 75 to 150° C. and pressures from about 50 to 3000 psig. The mixtures to be hydrogenated may contain ammonia, caustic or solvents such as methanol, tetrahydrofuran, dioxane, butanol and/or isopropanol.

Although the presence of a strongly basic material in the reaction mixture of the present process is not essential, the addition of a strong base increases the reaction rate of the process. Strongly basic materials that may be used to increase the reaction rate of the present process include water soluble alkali metal hydroxides, alkaline earth metal hydroxides, tertiary amines including 1,3-dimethylpiperidine, triethylamine and pyridine, Lewis bases, strongly basic ion exchange resins and basic aluminas and zeolites. An example of a strongly basic ion exchange resin is AMBERLYST A26 ion exchange resin available from Rohm & Haas. A preferred Lewis base for the present process is KF.

The present process may also be carried out with a solvent present, alone or in combination with water, in the reaction mixture. Such solvent needs to be inert under the reaction conditions of the process. That is the solvent should not be a material or mixture that will add or otherwise react non-reversibly with the subject pentenenitriles. Preferred solvents include dioxane, tetrahydrofuran, dimethylformamide, dimethylacetamide, methanol, butanols and isopropanol. If a solvent is used in the reaction mixture, it is preferred that the solvent is combined with water and that the concentration of water in the reaction mixture be between 15 and 60% by weight. This concentration of water aids in maintaining a good reaction rate and good selectivity to the desired product. The present process, even without the addition of a solvent (for example, the reaction could be run in a liquid alkylamine or be run under pressure), has a faster rate and improved selectivity if it is run in the presence of water. It is preferred that the concentration of the water in the reaction mixture be between about 15 and 60% by weight. Water need not be present in the reaction mixture for the reaction of the present process to take place although the presence of water is beneficial to the process.

The reaction of the present process is carried out at temperatures from about 25 to 200° C. and at pressures from autogeneous to pressures of about 1500 psig. Typically the autogeneous pressure of the present process may reach a pressure of about 1000 psig. The present reaction may be run as a continuous reaction, for example, using a continuous stirred tank reactor, a trickle bed or a plug-flow reactor, or as a batch reaction.

The weight ratio of 3-pentenenitrile to 4-pentenenitrile in the present process may be from 0 to 1 to 1 to 0. The preferred molar ratio of ammonia or alkylamine to pentenenitrile for the present process is from 0.3 to 3, and it is 0.15 to 1.5 for hydrazine to pentenenitrile. Either the cis or trans isomers of the 3-pentenenitrile may be used in the present process.

The present process allows the cyanobutylation of ammonia or an alkylamine. Alkylamines suitable for the present process include the class consisting of alkylamines having from 1 to 10 carbon atoms, dimethylamine, dodecylamine, ethylenediamine, 2-methyl-pentamethylenediamine, 1,3-diaminopentane, 1,2-diaminocyclohexane, 3-methylpiperidine, octadecylamine, hexamethylenediamine, and piperazine.

Some reaction products formed by the present process include reaction products which have the formula:

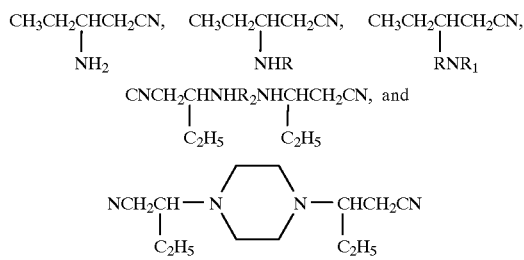

where R and $R_1$ are alkyl or alkylamino groups and $R_2$ is alkylene.

The following examples illustrate the present invention, but are not intended to limit the invention.

EXAMPLES

Example 1
Cyanobutylation of Ammonia with a Mixture of 3- and 4-Pentenenitrile in Water Fifty grams of a mixture containing 68.4% by weight 3-pentenenitrile and 12.6% by weight 4-pentenenitrile were charged into a 300 ml stainless steel batch stirred autoclave under nitrogen. To the autoclave was also added 50 g of aqueous 29% ammonia at room temperature. The autoclave was sealed and heated to 100° C. with minimal stirring. At reaction temperature, maximum stirring of 1400 rpms commenced. The reaction was run in the batch mode at autogeneous pressure for 3 hours. The reaction contents were cooled to room temperature and transferred to a separatory funnel. After 1 hour, the layers were separated and analyzed by gas chromatography on a 50 meter×0.53 mm DB-1701 glass capillary column. The conversion of 3-pentenenitrile and 4-pentenenitrile was 41.7% and 92.9%, respectively yielding 3-aminopentanenitrilenitrile in a selectively of 90%.

Example 2
Cyanobutylation of Ammonia with trans-3-Pentenenitrile in Water

Forty grams of 95.8% by weight trans-3-pentenentrile was charged into a 300 ml stainless steel batch stirred autoclave under nitrogen. To the autoclave was also added 37.6 g of aqueous 29% ammonia at room temperature. The autoclave was sealed and heated to 110° C. with minimal stirring. At reaction temperature, maximum stirring of 1400 rpms commenced. The reaction was run in a batch mode at autogeneous pressure for 5 hours. The reaction contents were cooled to room temperature and transferred to a separatory funnel. After 1 hour, the layers were separated and analyzed by gas chromatography on a 50 meter×0.53 mm DB-1701 glass capillary column. The conversion of trans-3-pentenenitrile was 32.6% yielding 3-aminopentanenitrile in a selectively of 79.4%.

Example 3
Cyanobutylation of Methylamine with trans-3-Pentenenitrile in Water

Forty grams of a mixture containing 95.8% by weight 3-pentenenitrile was charged into a 300 ml stainless steel batch stirred autoclave under nitrogen. To the autoclave was also added 49 g of aqueous 40% methylamine at room temperature. The autoclave was sealed and heated to 90° C. with minimal stirring. At reaction temperature, maximum stirring of 1400 rpms commenced. The reaction was run in the batch mode at autogeneous pressure for 5 hours. The reaction contents were cooled to room temperature yielding a homogeneous solution. The product was analyzed by gas chromatography on a 50 meter×0.53 mm DB-1701 glass capillary column. The conversion of 3-pentenenitrile was 95.6% yielding 3-methylaminopentanenitrile in a selectively of 95.3%.

Example 4
Cyanobutylation of Ammonia with trans-3-Pentene-nitrile in Water Containing 1,3-Dimethylpiperidine Forty grams of 95.8% trans-3-pentenenitrile and 0.8 grams of 1,3-dimethylpiperidine were charged into a 300 ml stainless steel batch stirred autoclave under nitrogen. To the autoclave was also added 37.6 grams of aqueous ammonia (29% by weight $NH_3$) while the autoclave was at room temperature.

The autoclave was then sealed and heated to 110° C. with minimal stirring. On reaching the reaction temperature stirring at a rate of 1400 rpms was commenced. The reaction was run in a batch mode for 5 hours at autogeneous pressure. The reaction mixture was then cooled to room temperature and transferred to a separatory funnel. After 1 hour, the layers were separated and analyzed by gas chromatography on a 50 meter×0.53 mm DB-1701 glass capillary column. The conversion of trans-3-pentenenitrile was 56.9% yielding 3-aminopentanenitrile and cis and trans-2-pentenenitrile at a selectivity of 81.1% and 12%, respectively.

Example 5
Cyanobutylation of Ammonia with trans-3-Pentene-nitrile in Water Containing AMBERLYST A26 Ion Exchange Resin Forty grams of 95.8% trans-3-pentenenitrile and 4.0 grams of AMBERLYTE A26 (strongly basic microreticular ion exchange resin from Rohm & Haas Co.) were charged into a 300 ml stainless steel batch stirred autoclave under nitrogen. To the autoclave was also added 37.6 grams of aqueous ammonia (29% by weight $NH_3$) while the autoclave was at room temperature.

The autoclave was then sealed and heated to 110° C. with minimal stirring. On reaching the reaction temperature stirring at a rate of 1400 rpms was commenced. The reaction was run in a batch mode for 5 hours at autogeneous pressure. The reaction mixture was then cooled to room temperature and transferred to a separatory funnel. After 1 hour, the layers were separated and analyzed by gas chromatography on a 50 meter×0.53 mm DB-1701 glass capillary column. The conversion of trans-3-pentenenitrile was 52% yielding 3-aminopentanenitrile and cis and trans-2-pentenenitrile at a selectivity of 82.4% and 11.5%, respectively.

Example 6
Batch Hydrogenation of 3-Aminopentanenitrile with RANEY Cobalt Catalyst with Water and Caustic In a batch run 96 grams (0.89 mole, 99%) 3-aminopentanenitrile, 2 grams of water and 2.0 grams of a 5% by weight NaOH solution were charged into a 300 ml stainless steel autoclave equipped with a thermocouple, cooling coils, sample dip tube having a 5 micron stainless steel filter and an agitator with impeller blade. Such an autoclave is available form Autoclave Engineers. Following the charging of the NaOH and aminopentanenitrile, 2.0 grams (dry basis) of RANEY cobalt catalyst (RANEY 2724) was added to the mixture in the autoclave. The autoclave was then closed and purged 3 times with hydrogen. The temperature was then raised to 90° C. under 50 psig hydrogen pressure with very slow stirring. When the temperature of the mixture reached 90° C., the hydrogen pressure was increased to 800 psig and stirring at 1200 rpms was commenced. At these conditions of temperature and pressure the reduction of the aminopentanenitrile to 1.3-diaminopentane required 120 minutes.

The produce formed in the reaction was analyzed by gas chromatography and showed a yield of 99.5% 1,3-diaminopentane.

What is claimed is:

1. A process for making aliphatic 3-aminonitriles comprising the steps of forming a reaction mixture comprising 3-pentenenitrile, 4-pentenenitrile or mixtures of 3-pentenenitrile and 4-pentenenitrile and ammonia or an alkylamine or optionally forming the reaction mixture in the presence of water or incorporating water into the reaction mixture; and reacting the mixture at a temperature from about 25 to 200° C. and at pressures from autogeneous to pressures of about 1500 psig.

2. A process for making aliphatic 3-aminonitriles comprising the steps of forming a reaction mixture comprising 3-pentenenitrile, 4-pentenenitrile or mixtures of 3-pentenenitrile and 4-pentenenitrile, wherein the weight ratio of 3-pentenenitrile to 4-pentenenitrile is from 0 to 1 to 1 to about 0, with ammonia, an alkylamine or hydrazine, and a strong base or optionally forming the reaction mixtures in the presence of water or incorporating water into the reaction mixture; and reacting the mixture at a temperature from about 25 to 200° C. and at pressures from autogeneous to pressures of about 1500 psig.

3. The process of claim 2 wherein the alkylamine is selected from the class consisting of alkylamine having from 1 to 10 carbon atoms, dimethylamine, dodecylamine, ethylenediamine, 2-methylpentamethylene-diamine, 1,3-diaminopentane, 1,2-diaminocyclohexane, 3-methylpiperidine, octadecylamine, hexamethylenediamine, and piperazine.

4. The process of claim 2 wherein the molar ratio of ammonia or alkylamine to pentenenitrile is from 0.3 to 3 or the molar ratio of hydrazine to pentenenitrile is from 0.15 to 1.5.

5. The process of claim 2 wherein the reaction is carried out in the presence of a solvent.

6. The process of claim 1 wherein the reaction products have the formula:

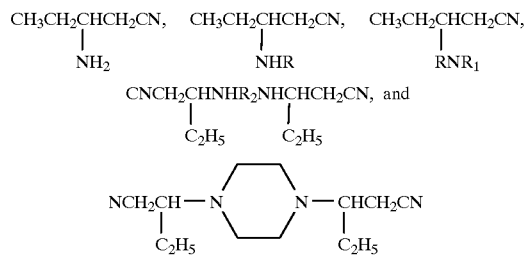

where R and $R_1$ are alkyl or alkylamino groups and $R_2$ is alkylene.

7. The process of claim 2 wherein the strong base is selected from the group consisting of water soluble alkali metal hydroxides; alkaline earth metal hydroxides, tertiary amines; Lewis bases, strongly basic ion exchange resins and basic aluminas and zeolites.

8. The process of claim 2 carried out as a continuous process.

9. The process of claim 2 carried out as a batch process.

10. The process of claim 2 wherein the concentration of water in the reaction mixture is from 15 to 60% by weight.

* * * * *